(12) United States Patent
She

(10) Patent No.: US 10,376,319 B2
(45) Date of Patent: Aug. 13, 2019

(54) IMAGE CORRECTION DESIGN SYSTEM AND METHOD FOR ORAL AND MAXILLOFACIAL SURGERY

(71) Applicant: Cheng Xin She, Kaohsiung (TW)

(72) Inventor: Cheng Xin She, Kaohsiung (TW)

( * ) Notice: Subject to any disclaimer, the term of this patent is extended or adjusted under 35 U.S.C. 154(b) by 0 days.

(21) Appl. No.: 15/580,730

(22) PCT Filed: Jun. 9, 2015

(86) PCT No.: PCT/CN2015/081083
§ 371 (c)(1),
(2) Date: Dec. 8, 2017

(87) PCT Pub. No.: WO2016/197326
PCT Pub. Date: Dec. 15, 2016

(65) Prior Publication Data
US 2018/0147015 A1    May 31, 2018

(51) Int. Cl.
*G16H 30/40*        (2018.01)
*A61B 34/10*        (2016.01)
(Continued)

(52) U.S. Cl.
CPC .............. *A61B 34/10* (2016.02); *A61B 6/14* (2013.01); *G06K 9/6202* (2013.01); *G06T 5/002* (2013.01);
(Continued)

(58) Field of Classification Search
CPC ...... A61C 13/0004; A61C 9/004; A61C 13/08; A61C 7/002; A61B 1/24; A61B 6/14;
(Continued)

(56) References Cited

U.S. PATENT DOCUMENTS

2006/0228010 A1* 10/2006 Rubbert ................... A61C 7/00
                                                             382/128
2008/0153067 A1*  6/2008 Berckmans .......... A61C 8/0001
                                                             433/213
(Continued)

*Primary Examiner* — Jingge Wu
(74) *Attorney, Agent, or Firm* — Raymond Y. Chan; David and Raymond Patent Firm

(57) ABSTRACT

An image correction design system for an oral and maxillofacial surgery. The image correction design system comprises: a first image data scanning module for scanning to obtain image data of relative coordinate positions of maxillofacial bones, teeth, and soft tissues; a second image data scanning module for scanning image data of a plaster dental impression of a patient; a scanning image correction and comparison module for correcting and comparing the image data from the first image data scanning module and the image data from the second image data scanning module and performing archiving to obtain first archives; an image block calculation module for performing an image layer management and block cutting display of the first archives to obtain second archives; a surgery simulation image design module for inputting a surgery data parameter for the second archives after the image layer management and cut block display, so as to design and establish surgery simulation image files; and an output module for outputting the surgery simulation image files by using a display device.

24 Claims, 20 Drawing Sheets

(51) Int. Cl.
*A61B 6/14* (2006.01)
*G06K 9/62* (2006.01)
*G06T 5/00* (2006.01)
*G06T 7/00* (2017.01)
*G16H 50/50* (2018.01)
*G16H 20/40* (2018.01)

(52) U.S. Cl.
CPC ........... *G06T 7/0014* (2013.01); *G16H 20/40* (2018.01); *G16H 30/40* (2018.01); *G16H 50/50* (2018.01); *A61B 2034/104* (2016.02); *A61B 2034/105* (2016.02); *G06T 2200/04* (2013.01); *G06T 2207/10081* (2013.01); *G06T 2207/30036* (2013.01)

(58) Field of Classification Search
CPC . A61B 6/5235; A61B 2034/105; A61B 34/10; G06F 17/50; G06K 9/6202; G06T 2200/04; G06T 2207/30036; G06T 5/002; G06T 7/0014; G16H 20/40; G16H 34/10; G16H 30/40; G16H 50/50
See application file for complete search history.

(56) References Cited

U.S. PATENT DOCUMENTS

| | | | | |
|---|---|---|---|---|
| 2009/0187393 | A1* | 7/2009 | Van Lierde | A61C 1/084 703/11 |
| 2009/0291417 | A1* | 11/2009 | Rubbert | A61C 7/00 433/215 |
| 2011/0059413 | A1* | 3/2011 | Schutyser | A61B 5/1077 433/8 |
| 2012/0191421 | A1* | 7/2012 | Greenberg | A61C 7/002 703/1 |
| 2012/0201443 | A1* | 8/2012 | Mollemans | A61C 9/0046 382/131 |
| 2014/0188448 | A1* | 7/2014 | Getto | A61C 7/002 703/6 |
| 2015/0327958 | A1* | 11/2015 | Llop | A61C 13/0004 433/213 |
| 2015/0374460 | A1* | 12/2015 | Sachdeva | G06T 17/00 703/1 |
| 2016/0012182 | A1* | 1/2016 | Golay | G16H 40/20 705/3 |
| 2019/0060033 | A1* | 2/2019 | Kaza | A61C 7/002 |

* cited by examiner

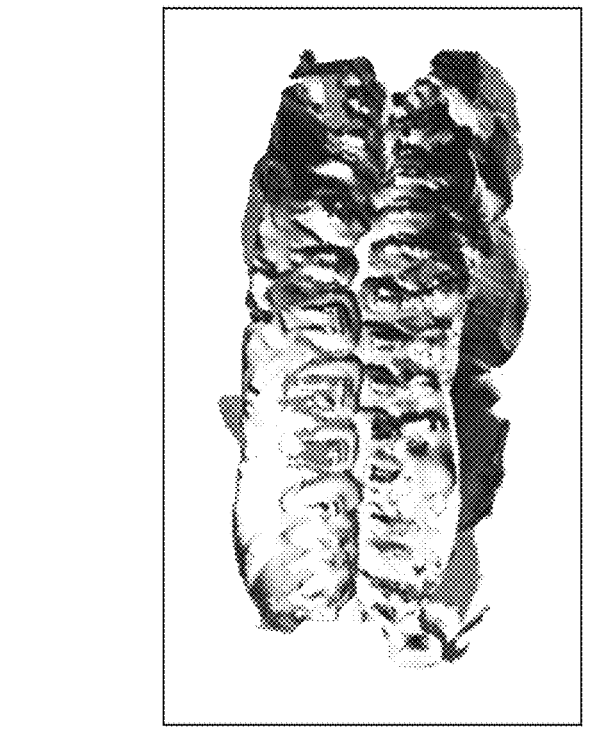
(b)
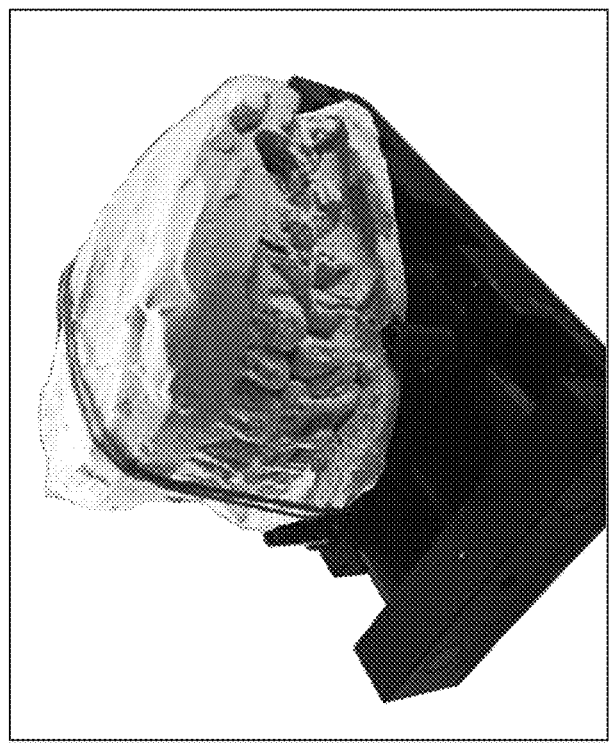
(a)
FIG.14

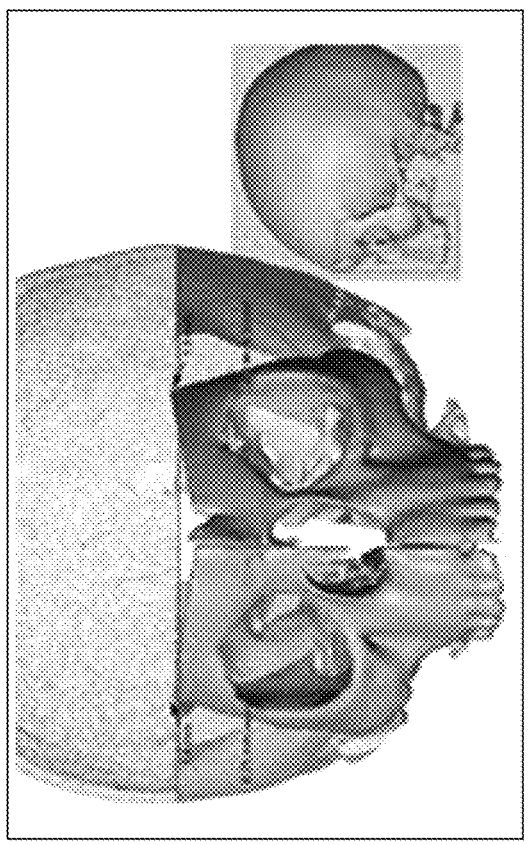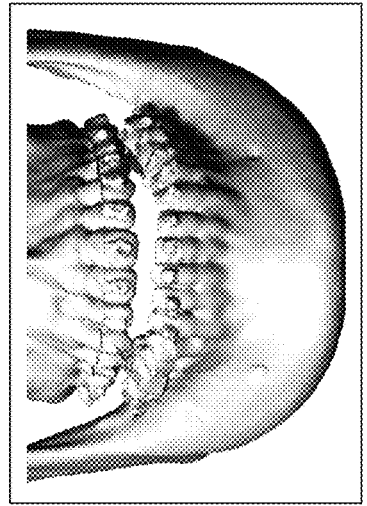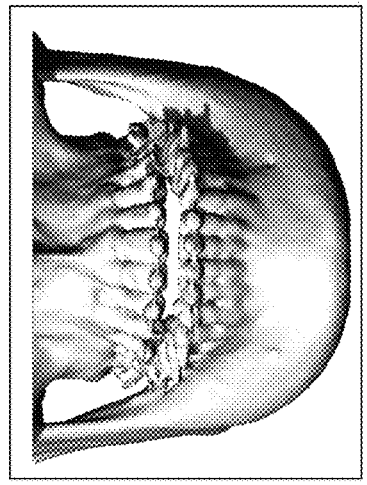
FIG.15

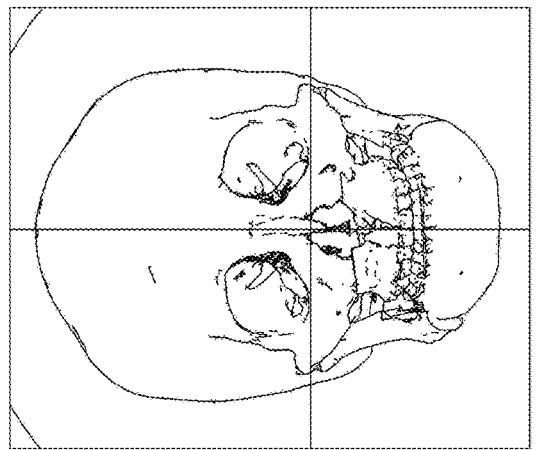
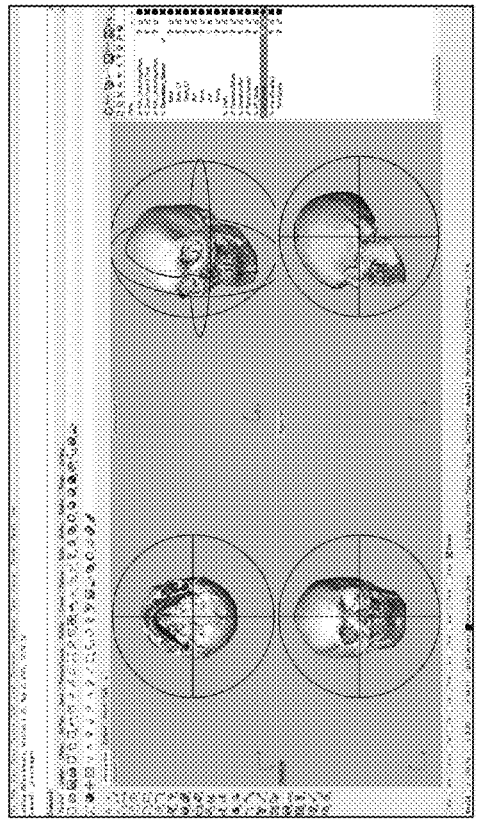
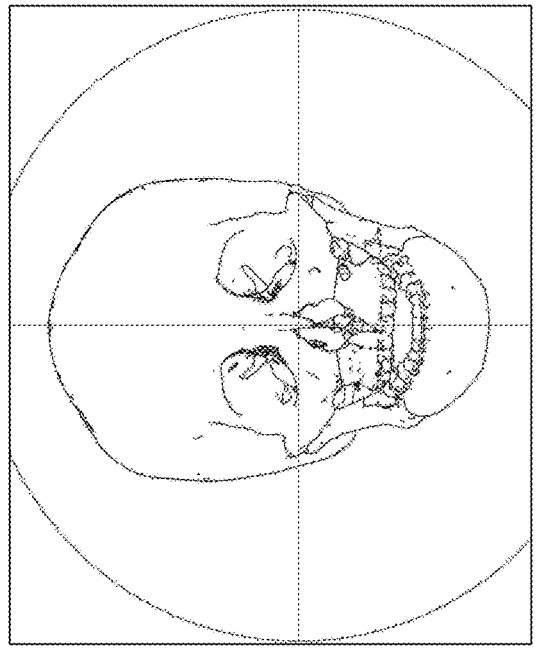
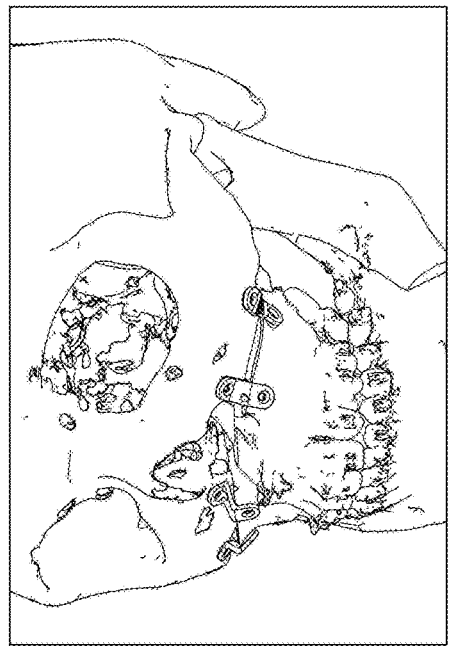
FIG. 16

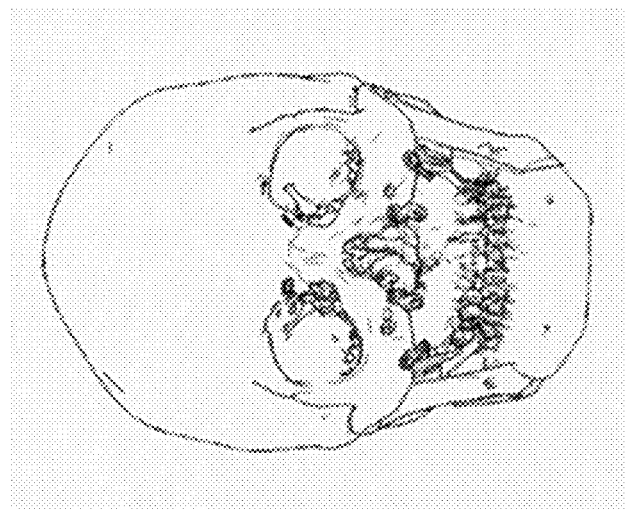
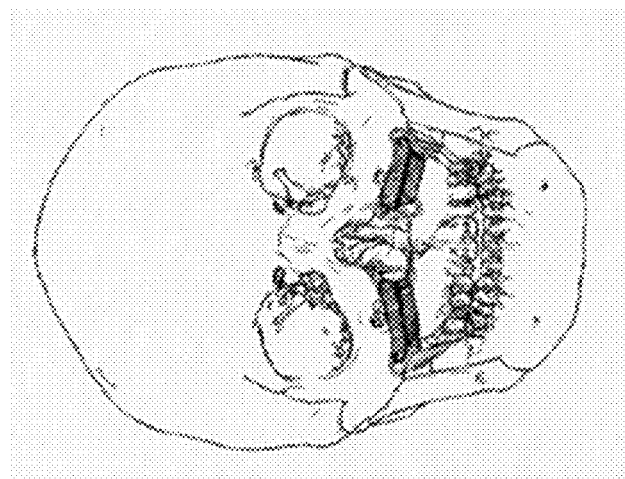
FIG19

# IMAGE CORRECTION DESIGN SYSTEM AND METHOD FOR ORAL AND MAXILLOFACIAL SURGERY

CROSS REFERENCE OF RELATED APPLICATION

This is a U.S. National Stage under 35 U.S.C. 371 of the International Application Number PCT/CN2015/081083, filed Jun. 9, 2015. The afore-mentioned patent application is hereby incorporated by reference in its entirety.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

This invention generally relates to an image correction design system and method for an oral and maxillofacial surgery, especially to an image correction design system and method for a dental, orthognathic and facial plastic surgery.

Description of Related Arts

Orthognathic surgery is surgery designed to correct conditions of the jaw and face related to structure, growth, sleep apnea, TMJ disorders, malocclusion problems owing to skeletal disharmonies, or other orthodontic problems that cannot be easily treated with braces. This surgery is also used to treat a patient with congenital cleft palate.

During an orthognathic surgery, bone of a patient is cut and adjusted by a physician, and then a bone plate and bone nails are joined to the skeleton and performing shaping. Typically as the orthognathic surgery is performed by a physician, a clinic file of X-ray machine or computerized tomography (CT) scan of a patient is needed to confirm a predetermined operation site, and a dental impression and correction for the surgery portion are performed according to the experience of the physician. In addition, in order to facilitate the fixation of the jaws or skeleton, a physician usually needs to use a medical metal bone plate, screws, bone nails, stainless steel wire and other materials for fixing and shaping the structure of the patient's jaws and face.

However, the common medical photographic equipment used in an oral and maxillofacial surgery cannot provide a correct image data accurately for simulation assessment before surgery or healing over confirmation after surgery to a physician. Generally, an orthognathic surgery is performed by a physician only according to the photographs taken by the current situation and the experience accumulated by the physician for years. The photographs are not true to the original that may cause misjudgment of the surgery portion and a prolongation of surgery time. Also, it fails to provide a physician with a comparing basis for tracking healing and preoperative assessment in real time during corrective treatment after surgery. In addition, it is possible to cause disadvantages of malocclusion that a patient fails to have a correct occlusion or has an excessive occlusion. Therefore, the experience and skills of physicians are often important factors in determining the success or failure of these operations.

Taiwan Patent No. 1367745 entitled "3D planning and prediction method for optimizing facial skeleton symmetry in orthognathic surgery" discloses a way of the best global positioning evaluation for dental model navigation in surgical planning using the best symmetry plane method. Base on the precision of coordinate relationships among the image model, tracking system, and dental cast, osteotomy prediction for jaw correction surgery can be achieved by assessing the symmetry degree in both oral and maxillofacial regions. Cephalometric analysis and evaluation of orthognathic surgery are elevated from two dimensions to three dimensions in order to compromise both oral functional restoration and aesthetics requirements. However, the planning and prediction method for optimizing facial skeleton symmetry fails to solve the problem that image is affected by noise and other interference factors, so that the converted file is not true to the original or the image is vague to cause misjudgment, and thus it cannot provide a correct image data accurately for simulation assessment before surgery or healing over confirmation after surgery by a physician.

Taiwan Patent No. 1397402 entitled "an integration method of dental implant positioning and implant guide planning" discloses an integrated method of implant position planning and drilling guide generation for dental implant. The method is based on patient's jaw models reconstructed from CT images and combines with his own dynamic occlusion surface. The optimal entry point of the implant can either be determined by patient's occlusal surface or the moment of inertia of the jawbone in order to obtain a possible position of the implant automatically. The planning process takes into account several crucial lengths, in terms of safety distances, between the skull boundary, the nerve, and the implants, and could be fabricated by rapid prototyping machine. The design of the guide template solves the undercut interference when mount the guide plate on teeth, and also take into consideration mouth opening distance and clinical issues in order to build high precision and accuracy drill guide plate using in dental implant. However, the above method still has accuracy problem of the CT images and patient's jaw models. It's possible to cause disadvantages of malocclusion that a patient fails to have a correct occlusion or has an excessive occlusion.

Taiwan Patent No. 1385606 entitled "method of locating and correcting a solid model of teeth and jaws and fixture thereof" discloses a method of locating and correcting a solid model of teeth and jaws, comprising a selecting step, a scanning step, a manufacturing step, a placing step, a positioning step and a correcting step. A teeth and jaws solid model is used as a standard model and a target tooth is selected to make a fixture according to the preceding steps, and the fixture is arranged on the corresponding teeth of a model to be corrected, and a positioning system, a positioning plate and a handheld positioning machine with a positioning mark are used to perform positioning and correction. The positioning and correction can be performed for every tooth respectively by the above steps. However, the above method cannot scan the skeleton image accurately and provide positioning, and thus it cannot provide a correct image data accurately for simulation assessment before surgery or healing over confirmation after surgery by a physician.

In summary, it is necessary to propose an image correction design system and method for an oral and maxillofacial surgery that can be applied to a dental, orthognathic and facial plastic surgery, and can accurately provide a correct image data to a physician to do a simulated preoperative assessment or postoperative healing confirmation to shorten the time of surgery and improve the success rate of these operations.

SUMMARY OF THE PRESENT INVENTION

The main purpose of the invention is to provide an image correction design method for an oral and maxillofacial surgery. The method can be used in dental, orthognathic and facial plastic surgery. According to an image correction design method for an oral and maxillofacial surgery of the invention, since a process of correction and comparison of scanning images is executed, the time for performing the dental, orthognathic and facial plastic surgery can be shortened, and the features of human skeleton of surgery is simulated to position the skeleton and a correction appliance accurately and combine firmly after surgery.

Another main purpose of the invention is to provide an image correction design system for an oral and maxillofacial surgery, wherein a scanning image correction and comparison module is used for correcting and comparing the image data from the first image data scanning module and the image data from the second image data scanning module so that the image correction design system for an oral and maxillofacial surgery can have effect of accurately positioning an operation site before surgery and accurately positioning a fixing plate combining with the skeleton after surgery.

To achieve the above purpose, the invention provides an image correction design method for an oral and maxillofacial surgery. The image correction design method comprises steps of: inputting a first scanning image data for scanning to obtain image data of relative coordinate positions of maxillofacial bones, teeth, and soft tissues; inputting a second scanning image data for scanning image data of a plaster dental impression of a patient; executing correction and comparison of scanning images for correcting and comparing the first scanning image data and the second scanning image data and performing archiving to obtain first archives; performing an image block calculation for performing an image layer management and block cutting display of the first archives to obtain second archives; executing a surgery simulation image design for inputting a surgery data parameter for the second archives after the image layer management and cut block display, so as to design and establish surgery simulation image files; and outputting the surgery simulation image files by using a display device.

Preferably, the image correction design method for an oral and maxillofacial surgery further comprises a step of executing image data conversion used for converting the first scanning image data and the second scanning image data to 3 dimension data files.

Preferably, the image correction design method for an oral and maxillofacial surgery further comprises a step of executing image data conversion after the step of inputting a first scanning image data, and the step of executing image data conversion is used for converting the first scanning image data to a 3 dimension data file.

Preferably, for an image correction design method for an oral and maxillofacial surgery, the 3 dimension data file has a format of a 3 dimension (3D) mechanical design STL file.

Preferably, for an image correction design method for an oral and maxillofacial surgery, the first scanning image data is a computerized tomography scan file (CT file).

Preferably, for an image correction design method for an oral and maxillofacial surgery, the second scanning image data is an image data of a plaster dental impression of a patient scanned by a high precise grating instrument.

Preferably, the image correction design method for an oral and maxillofacial surgery further comprises a step of removing noise after step of correction and comparison of scanning images, and the step of removing noise is used for removing noise in the archive.

Preferably, the image correction design method for an oral and maxillofacial surgery further comprises a step of a bone plate correction for performing a comparison of the surgery simulation image file and the step of the bone plate correction.

Preferably, for the image correction design method for an oral and maxillofacial surgery, the step of a bone plate correction comprises a step of a surgery guiding bone plate correction and a step of a fixing bone plate correction.

Preferably, the step of a surgery guiding bone plate correction provides a correction for surgery cutting area and an accurate position correction of a surgery guiding bone plate.

Preferably, the step of a fixing bone plate correction provides an accurate position of a fixing bone plate for skeleton healing over after surgery and the correction for the determined position of the skeleton.

Preferably, for the image correction design method for an oral and maxillofacial surgery, the surgery data parameter is a moving distance of the oral and maxillofacial skeleton, an operation cutting angle or a skeleton overlap portion.

Preferably, for the image correction design method for an oral and maxillofacial surgery, the display device is a LCD, Tablet PC, PDA or smartphone.

To achieve the above another purpose, the invention provides an image correction design system for an oral and maxillofacial surgery. The image correction design system comprises: a first image data scanning module for scanning to obtain an image data of relative coordinate positions of maxillofacial bones, teeth, and soft tissues; a second image data scanning module for scanning to obtain an image data of a plaster dental impression of a patient; a scanning image correction and comparison module for correcting and comparing the image data from the first image data scanning module and the image data from the second image data scanning module and performing archiving to obtain first archives; an image block calculation module for performing an image layer management and block cutting display of the first archives to obtain second archives; a surgery simulation image design module for inputting a surgery data parameter for the second archives after the image layer management and cut block display, so as to design and establish surgery simulation image files; and an output module for outputting the surgery simulation image files by using a display device.

Preferably, the image correction design system for an oral and maxillofacial surgery further comprises an image data conversion module used for converting the image data of the first image data scanning module and the image data of the second image data scanning module to 3 dimension data files.

Preferably, for the image correction design system for an oral and maxillofacial surgery, the first image data scanning module further comprises an image data conversion module used for converting the image data of the first image data scanning module to a 3 dimension data file.

Preferably, for an image correction design system for an oral and maxillofacial surgery, the 3 dimension data file has a format of a 3 dimension (3D) mechanical design STL file.

Preferably, for an image correction design system for an oral and maxillofacial surgery, the image data of the first image data scanning module is a computerized tomography scan file (CT file).

Preferably, for an image correction design system for an oral and maxillofacial surgery, the image data of the second image data scanning module is an image data of a plaster dental impression of a patient scanned by a high precise grating instrument.

Preferably, for the image correction design system for an oral and maxillofacial surgery, the scanning image correction and comparison module further comprises a noise removing module used for removing noise in the archive.

Preferably, the image correction design system for an oral and maxillofacial surgery further comprises a bone plate correction module for performing a comparison of the surgery simulation image file and the data of the bone plate correction module.

Preferably, for the image correction design system for an oral and maxillofacial surgery, the bone plate correction module comprises a surgery guiding bone plate correction module and a fixing bone plate correction module.

Preferably, the surgery guiding bone plate correction module provides a correction for surgery cutting area and a position correction for accurately drilling holes on a surgery guiding bone plate.

Preferably, the fixing bone plate correction module provides an accurate position of a fixing bone plate for skeleton healing over after surgery and a correction for the determined position of the skeleton.

Preferably, for the image correction design system for an oral and maxillofacial surgery, the surgery data parameter is a moving distance of the oral and maxillofacial skeleton, an operation cutting angle or a skeleton overlap portion.

Preferably, for the image correction design method for an oral and maxillofacial surgery, the display device is a LCD, Tablet PC, PDA or smartphone.

BRIEF DESCRIPTION OF THE DRAWINGS

FIG. 14 shows a second scanning image data of an image correction design system for an oral and maxillofacial surgery of the invention.

FIG. 15 shows a view of correction and comparison of scanning images of an image correction design system for an oral and maxillofacial surgery of the invention.

FIG. 16 shows an image block calculation for performing an image layer management and block cutting display of an image correction design system for an oral and maxillofacial surgery of the invention.

FIG. 19 shows a view of correction and comparison of the surgery simulation image files and a bone plate of an image correction design system for an oral and maxillofacial surgery of the invention.

DETAILED DESCRIPTION OF THE PREFERRED EMBODIMENT

The following description is used to disclose the invention for being able to practice the invention by those of ordinary skill in the art. Preferred embodiments described in the following description is made only by way of example, and variations of those preferred embodiments may become apparent to the skilled artisans. The basic principles of the invention defined in the following description may be applied in the other embodiments, variations, modifications, equivalents of the embodiments and the other examples that are not departing from the spirit and scope of the invention.

Figure 1:
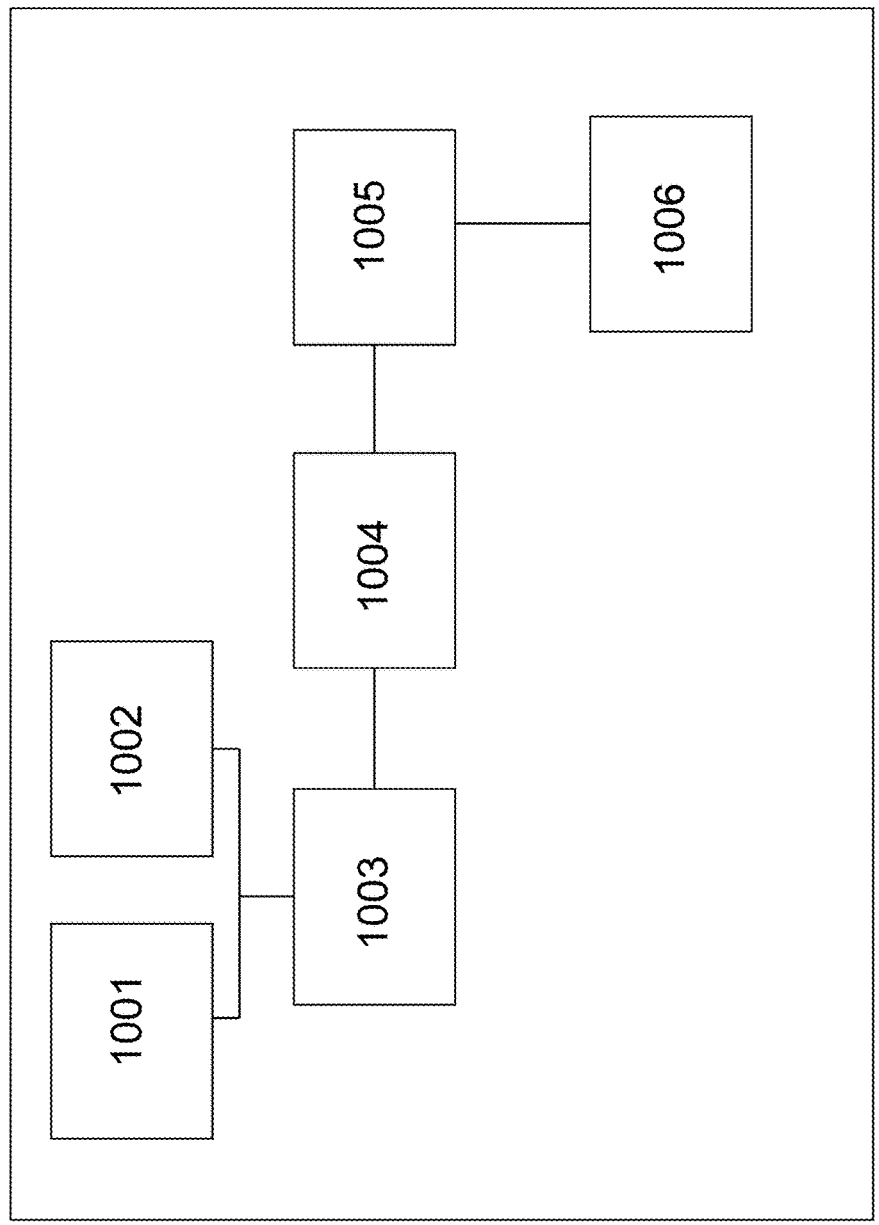
FIG. 1 shows a functional block diagram of a first embodiment of an image correction design system for an oral and maxillofacial surgery of the invention.

FIG. 1 shows a functional block diagram of a first embodiment of an image correction design system for an oral and maxillofacial surgery of the invention, wherein the image correction design system for an oral and maxillofacial surgery 1000 comprises: a first image data scanning module 1001; a second image data scanning module 1002; a scanning image correction and comparison module 1003; an image block calculation module 1004; a surgery simulation image design module 1005; and an output module 1006.

Figure 2:
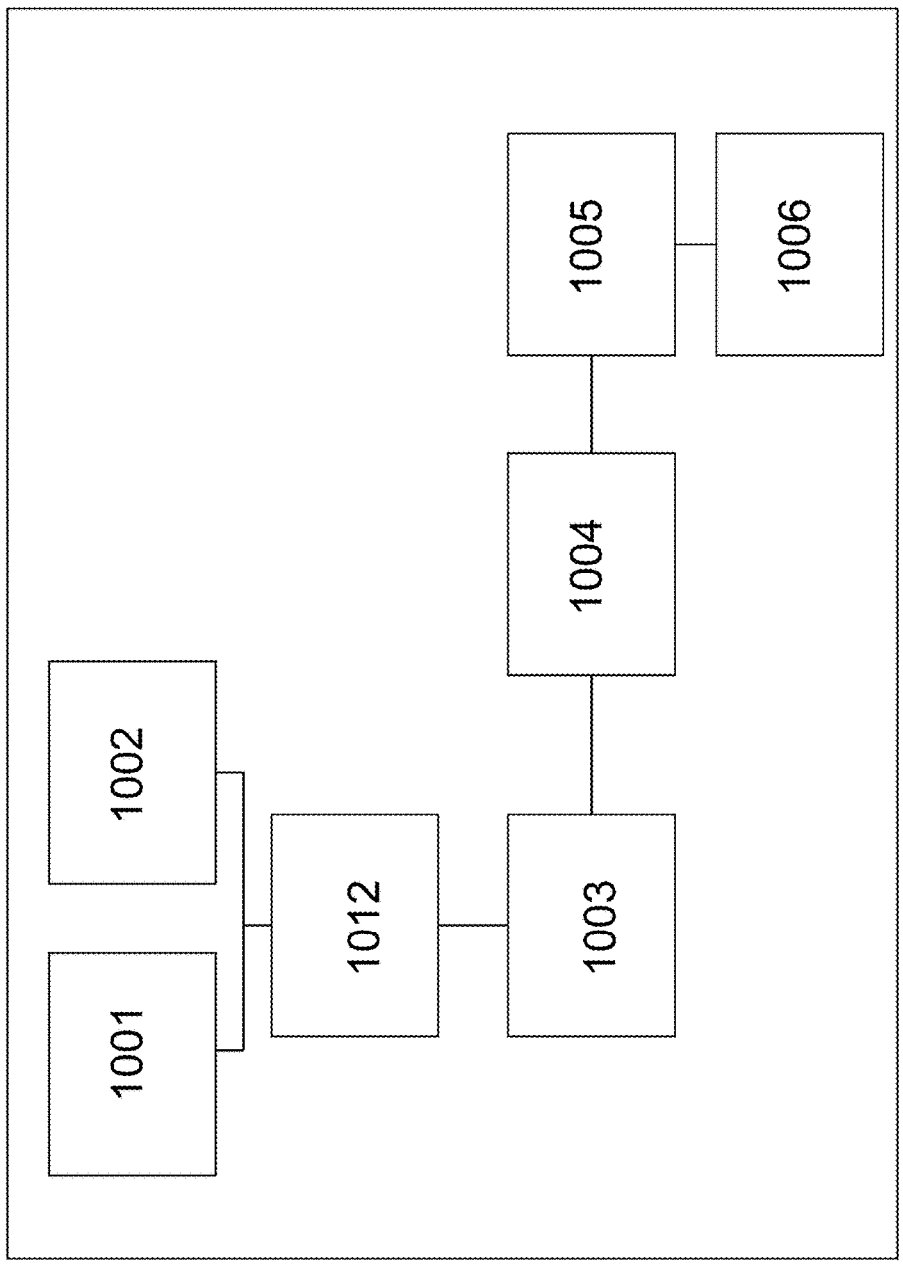
FIG. 2 shows a functional block diagram of a second embodiment of an image correction design system for an oral and maxillofacial surgery of the invention.
Figure 13:
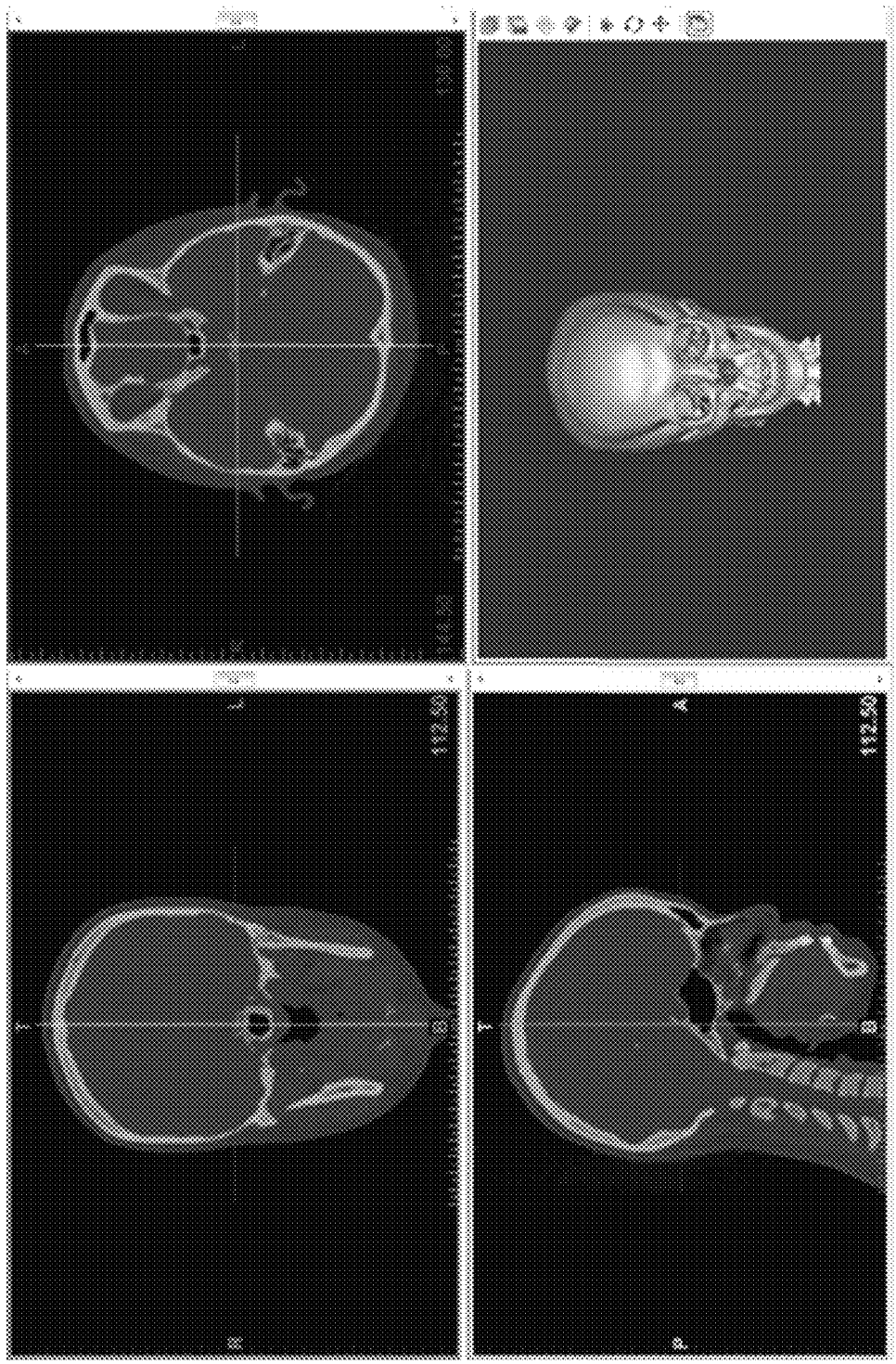
FIG. 13 shows a first scanning image data of an image correction design system for an oral and maxillofacial surgery of the invention.

FIG. 2 shows a functional block diagram of a second embodiment of an image correction design system for an oral and maxillofacial surgery of the invention. When an orthognathic surgery is performed by a physician, a clinic file of X-ray machine or computerized tomography (CT) scan is needed to confirm a predetermined operation site. An image correction design system for an oral and maxillofacial surgery 1000 can provide a correct and accurate image to a physician for reference. When an image correction design system for an oral and maxillofacial surgery 1000 is performed, starting the first image data scanning module 1001 is executed. The first image data scanning module 1001 is used for scanning to obtain image data of relative coordinate positions of maxillofacial bones, teeth, and soft tissues of a patient, wherein the first scanning image data is an image taken by X-ray machine or computerized tomography scan equipment, and the image is like a computerized tomography scan file (hereafter referred to as CT file). The first scanning image data is a computerized tomography scan file (CT file), and it is stored in the first image data scanning module 1001 of FIG. 13. Next, starting the second image data scanning module 1002 is executed. The second image data scanning module 1002 is used for scanning image data of a plaster dental impression of a patient, wherein the second scanning image data is shown in FIG. 14, wherein a plaster dental impression is provided for a patient by an orthodontic physician, and an occlusal dental impression before surgery and an orthognathic simulated occlusal dental impression after surgery of a patient are shown in FIG. 14(*a*). Also, the plaster dental impression of a patient is scanned by a high precise grating instrument to obtain a digital data of a patient's teeth shown as a file of FIG. 14(*b*), and the file is stored in the second image data scanning module 1002, wherein the image correction design system for an oral and maxillofacial surgery 1000 further comprises an image data conversion module 1012 for converting the first scanning image data such as Dicom file including bones, teeth and soft tissues that is stored in the first image data scanning module 1001 and the second scanning image data such as the digital image data of the plaster dental impression that is stored in the second image data scanning module 1002 to a 3 dimension (3D) data file, wherein the format of the 3 dimension (3D) data file may be further converted to a 3 dimension (3D) mechanical design STL file for using in a computerized 3D simulation drawing and analysis.

Following the above-mentioned second embodiment, for the image correction design system for an oral and maxillofacial surgery 1000, starting a scanning image correction and comparison module 1003 is executed. The image data from the first image data scanning module 1001 and the image data from the second image data scanning module 1002 are inputted in the scanning image correction and comparison module 1003 and image correction and comparison are performed, and the file compared is archived. FIG. 15 is a view of correction and comparison of scanning image of an image correction design system for an oral and maxillofacial surgery of the invention. FIG. 15(*a*) shows an image file of correction and comparison of jaws image. FIG. 15(*b*) is an image data of the first image data scanning module. As shown in FIG. 15(*b*), the image data is a 3 dimension (3D) data file which is converting from the CT file taken previously, wherein a teeth portion in the drawing is likely to be affected by noise, interference from reflecting the light and metal, etc., so that the converted file is not true to the original or the image is vague. Also, the second image data scanning module 1002 uses a high precise grating instrument to scan a plaster dental impression of a patient in order to obtain an image data of the teeth, and the image data of the teeth is converted through a 3 dimension (3D) data file. Also, the image data of the first image data scanning module 1001 that is a 3D file converted by CT may perform simulation and positioning of 3D position by a scanning image correction and comparison module 1003 in order to replace the teeth portion of the CT file of the previous first scanning image data to a dental impression image with a true size of the second scanning image data shown as in FIG. 15(*c*).

Following the above-mentioned second embodiment, for the image correction design system for an oral and maxillofacial surgery 1000, then an image block calculation module 1004 is executed. The archives shown as in FIG. 15(*c*) of the image corrected and compared by the scanning image correction and comparison module 1003 may perform an image layer management of surgery simulation and block cutting display calculation. A physician may use the image correction design system for an oral and maxillofacial surgery 1000 to simulate an operation site of the surgery in a computer, and an image layer management can be performed by separately displaying each portion that is cut according to the simulation surgery as the cutting block shown in FIG. 16, and after separately displaying, a comparison calculation is performed by aligning a lower jaw portion which is cut open to an occlusal position of the image of the dental impression after the simulation surgery that is provided by an orthodontic physician.

Figure 17:
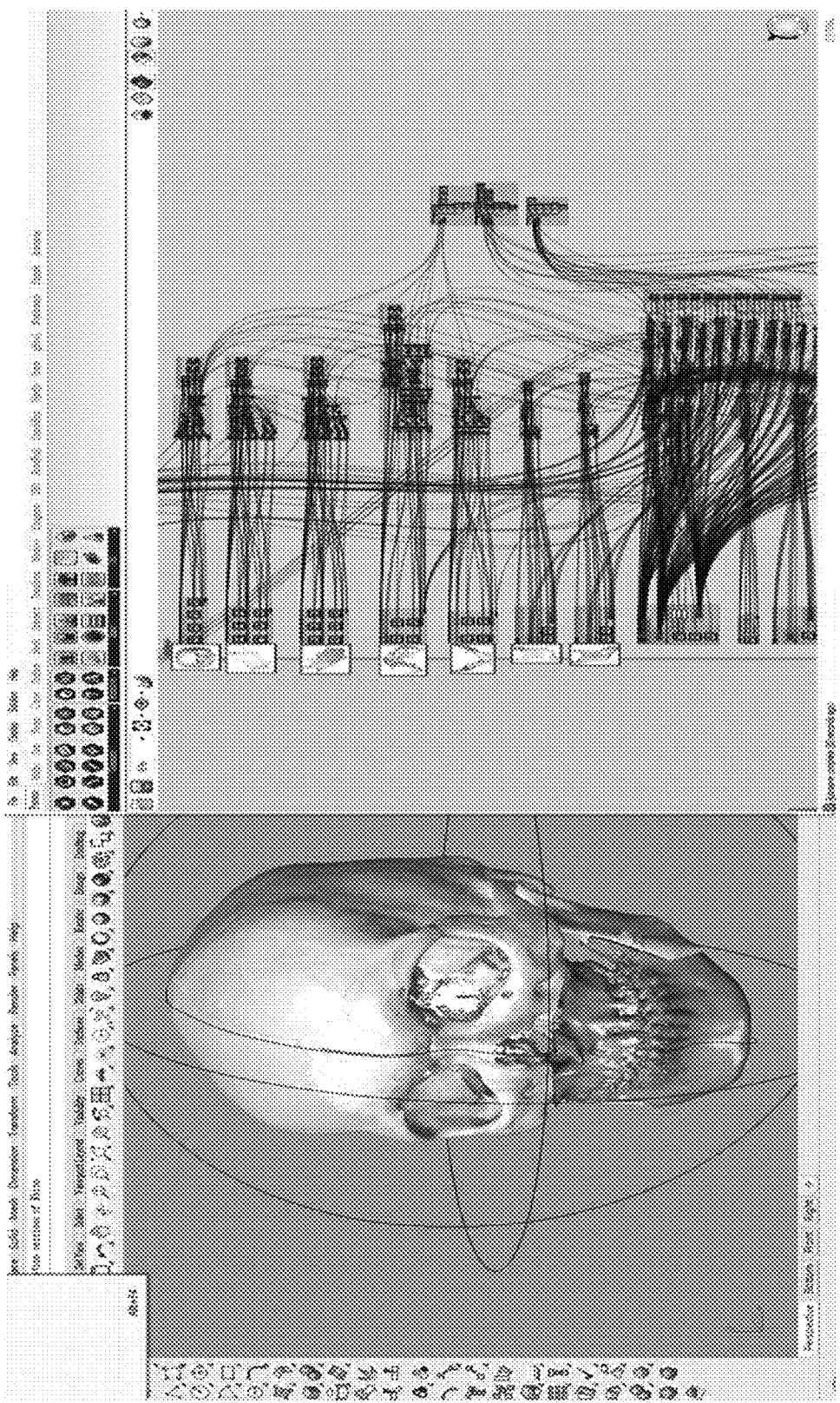
FIG. 17 shows a surgery simulation image of inputting a surgery data parameter of an image correction design system for an oral and maxillofacial surgery of the invention.
Figure 20:
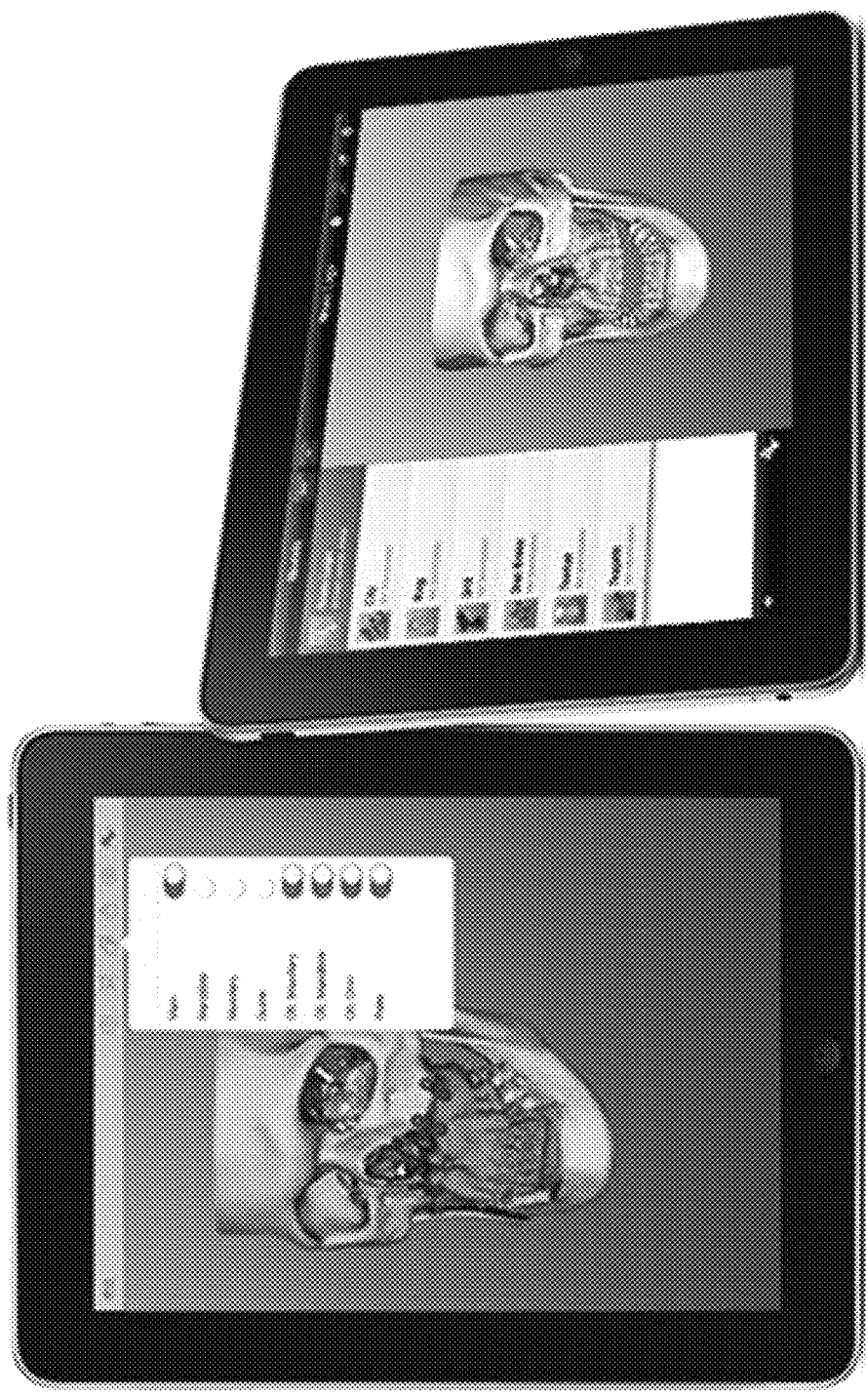
FIG. 20 is a display device used for outputting the surgery simulation image files of an image correction design system for an oral and maxillofacial surgery of the invention.

Following the above-mentioned second embodiment, for the image correction design system for an oral and maxillofacial surgery 1000, before the surgery is executed, a physician may use calculation data of a surgery simulation image design module 1005 to perform simulation comparison by inputting a surgery data parameter for the archives after the image layer management and cut block display of an image block calculation module 1004, so as to design and establish surgery simulation image files, wherein the surgery data parameter such as the related data of an operation site, skeleton moving distance, operation angle or dental impression overlap portion, etc., shown as in FIG. 17. Each portion that is cut according to the decision of a physician in the surgery and occlusal upper jaw and lower jaw required by an orthodontic physician are provided. Also, an output module 1006 is used for outputting the surgery simulation image files of a surgery simulation image design module 1005 by using a display device, shown as in FIG. 20. The physician can discuss with the orthodontic physician about the positions before and after surgery, and simulate the state after surgery. The display device is a LCD, Tablet PC, PDA or smartphone.

Figure 3:
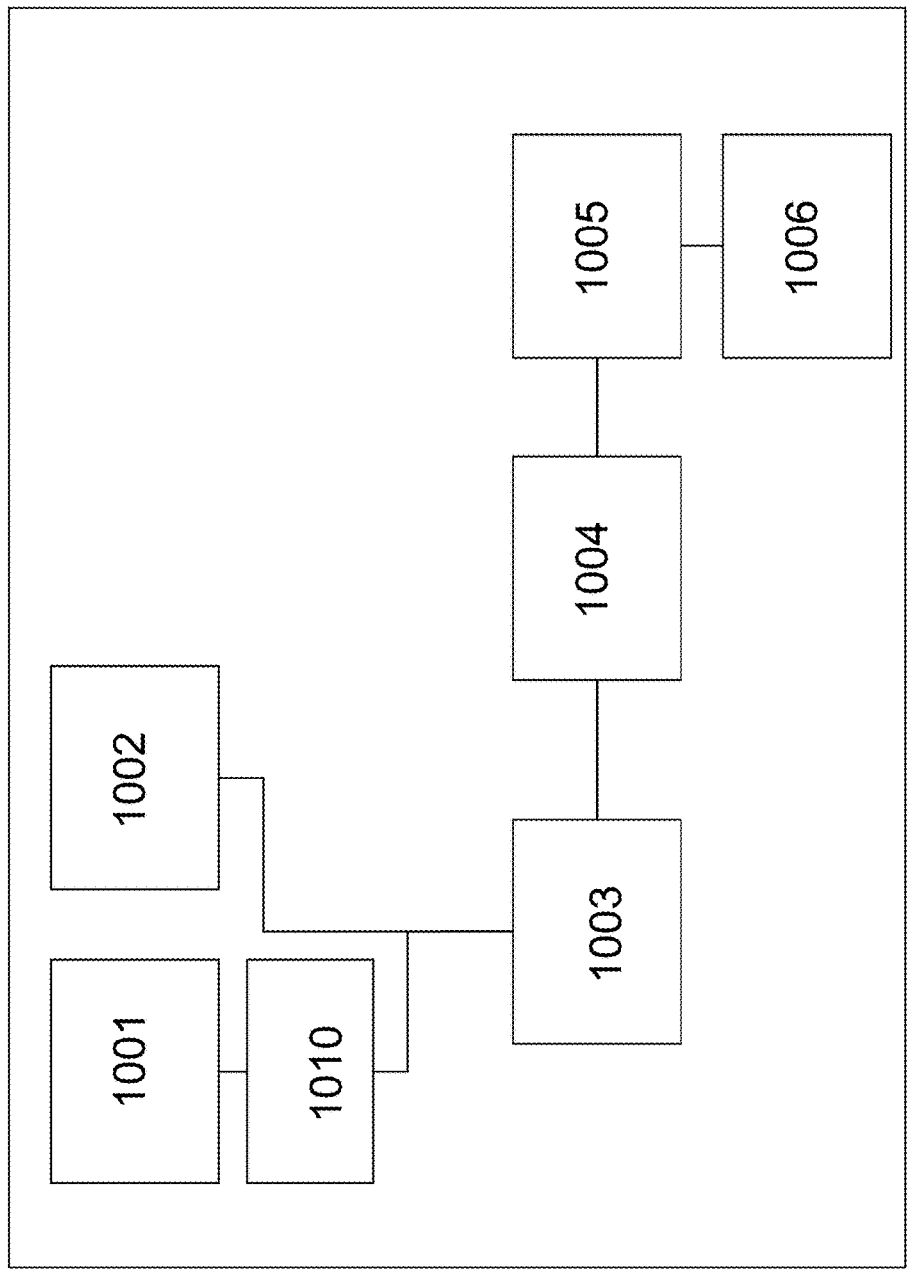
FIG. 3 shows a functional block diagram of a third embodiment of an image correction design system for an oral and maxillofacial surgery of the invention.

FIG. 3 shows a functional block diagram of a third embodiment of an image correction design system for an oral and maxillofacial surgery of the invention, wherein the image correction design system for an oral and maxillofacial surgery 1000 comprises: a first image data scanning module 1001; an image data conversion module 1010; a second image data scanning module 1002; a scanning image correction and comparison module 1003; an image block calculation module 1004; a surgery simulation image design module 1005; and an output module 1006.

Following the above-mentioned third embodiment, for an image correction design system for an oral and maxillofacial surgery 1000, a first image data scanning module 1001 further comprises an image data conversion module 1010 for converting the first scanning image data such as Dicom file including bones, teeth and soft tissues that is stored in the first image data scanning module 1001 to a 3 dimension (3D) data file, wherein the format of the 3 dimension (3D) data file may be further converted to a 3 dimension (3D) mechanical design STL file for using in a computerized 3D simulation drawing and analysis. Next, starting a scanning image correction and comparison module 1003 is executed. The first scanning image data from the image data conversion module 1010 and the image data from the second image data scanning module 1002 are inputted in the scanning image correction and comparison module 1003 and image correction and comparison are performed, and the file compared is archived. The second scanning image data is a 3 dimension (3D) data file. Next, the image block calculation module 1004, the surgery simulation image design module 1005, and an output module 1006 are executed with the same aspects as the above embodiments so the repeated description is omitted.

Figure 4:
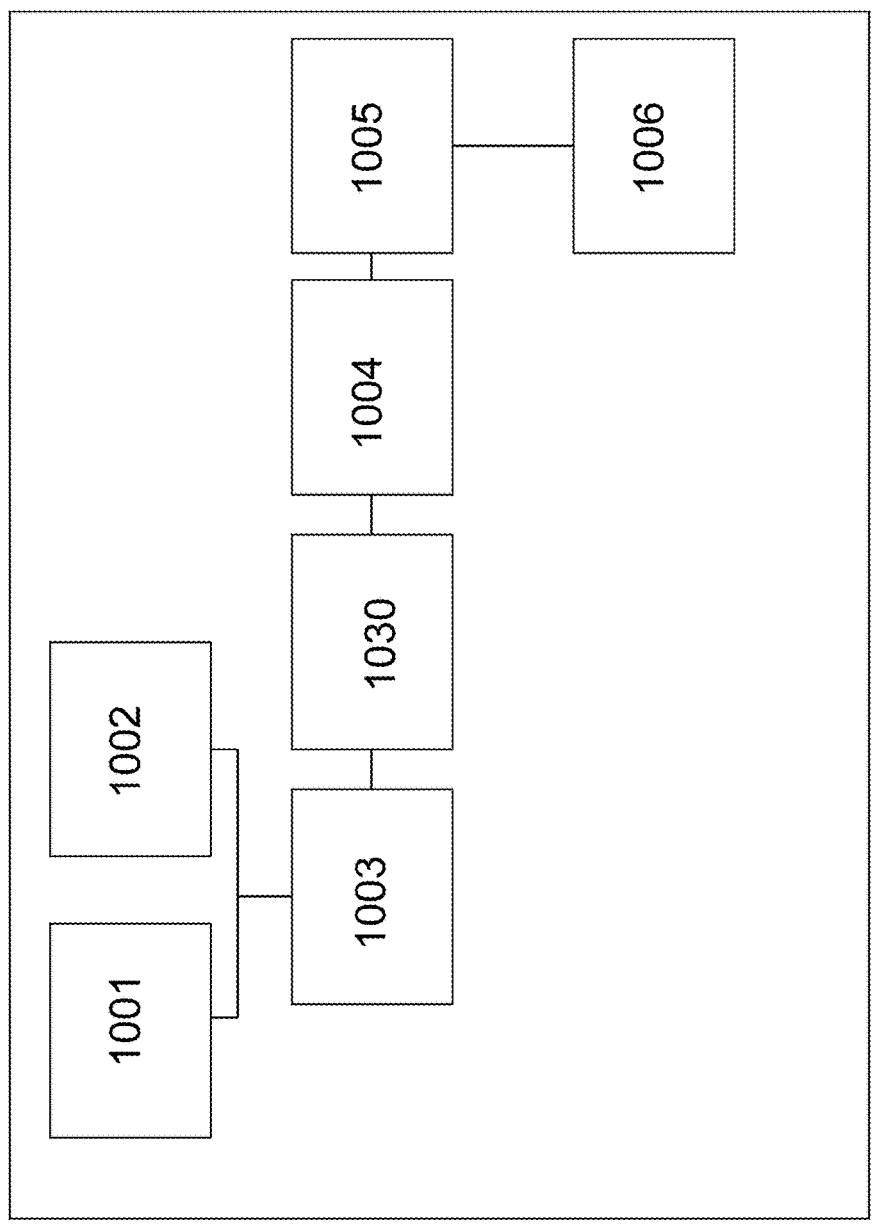
FIG. 4 shows a functional block diagram of a fourth embodiment of an image correction design system for an oral and maxillofacial surgery of the invention.

FIG. 4 shows a functional block diagram of a fourth embodiment of an image correction design system for an oral and maxillofacial surgery of the invention, wherein the image correction design system for an oral and maxillofacial surgery 1000 comprises: a first image data scanning module 1001; a second image data scanning module 1002; a scanning image correction and comparison module 1003; a noise removing module 1030; an image block calculation module 1004; a surgery simulation image design module 1005; and an output module 1006.

Following the above-mentioned fourth embodiment, for an image correction design system for an oral and maxillofacial surgery 1000, starting a scanning image correction and comparison module 1003 is executed. The image data from the first image data scanning module 1001 and the image data from the second image data scanning module 1002 are inputted in the scanning image correction and comparison module 1003 and image correction and comparison are performed, and the file compared is archived, wherein the images treated by the scanning image correction and comparison module 1003 are likely to be affected by noise and other interference factors, so that the converted file is not true to the original or the image is vague. Therefore, the scanning image correction and comparison module 1003 further comprises a noise removing module 1030 for removing noise in the archive to obtain a true image data. Next, the image block calculation module 1004, the surgery simulation image design module 1005, and an output module 1006 are executed with the same aspects as the above embodiments so the repeated description is omitted.

Figure 5:
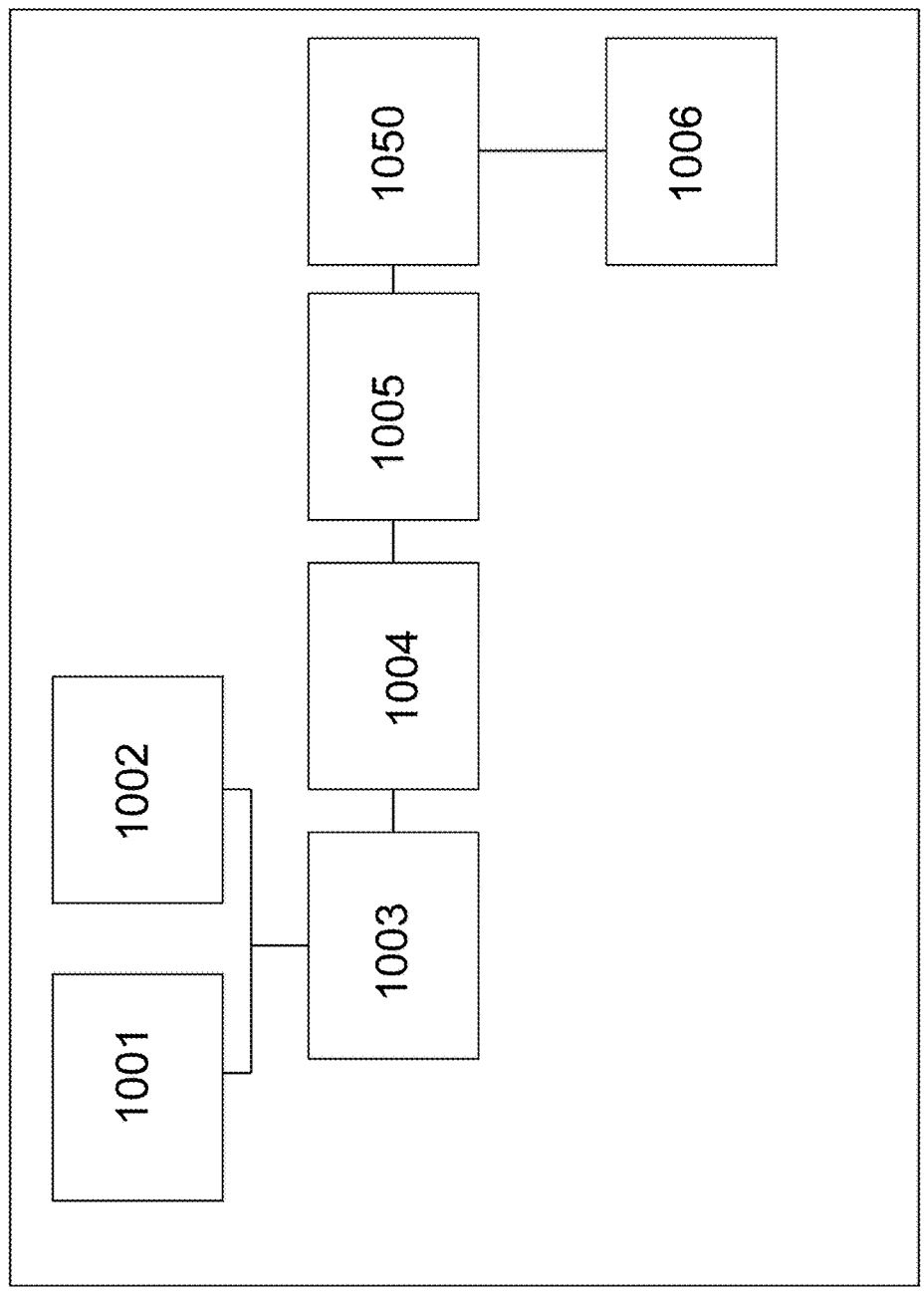
FIG. 5 shows a functional block diagram of a fifth embodiment of an image correction design system for an oral and maxillofacial surgery of the invention.

FIG. 5 shows a functional block diagram of a fifth embodiment of an image correction design system for an oral and maxillofacial surgery of the invention, wherein the image correction design system for an oral and maxillofacial surgery 1000 comprises: a first image data scanning module 1001; a second image data scanning module 1002; a scanning image correction and comparison module 1003; a noise removing module 1030; an image block calculation module 1004; a surgery simulation image design module 1005; a bone plate correction module 1050; and an output module 1006.

Figure 18:
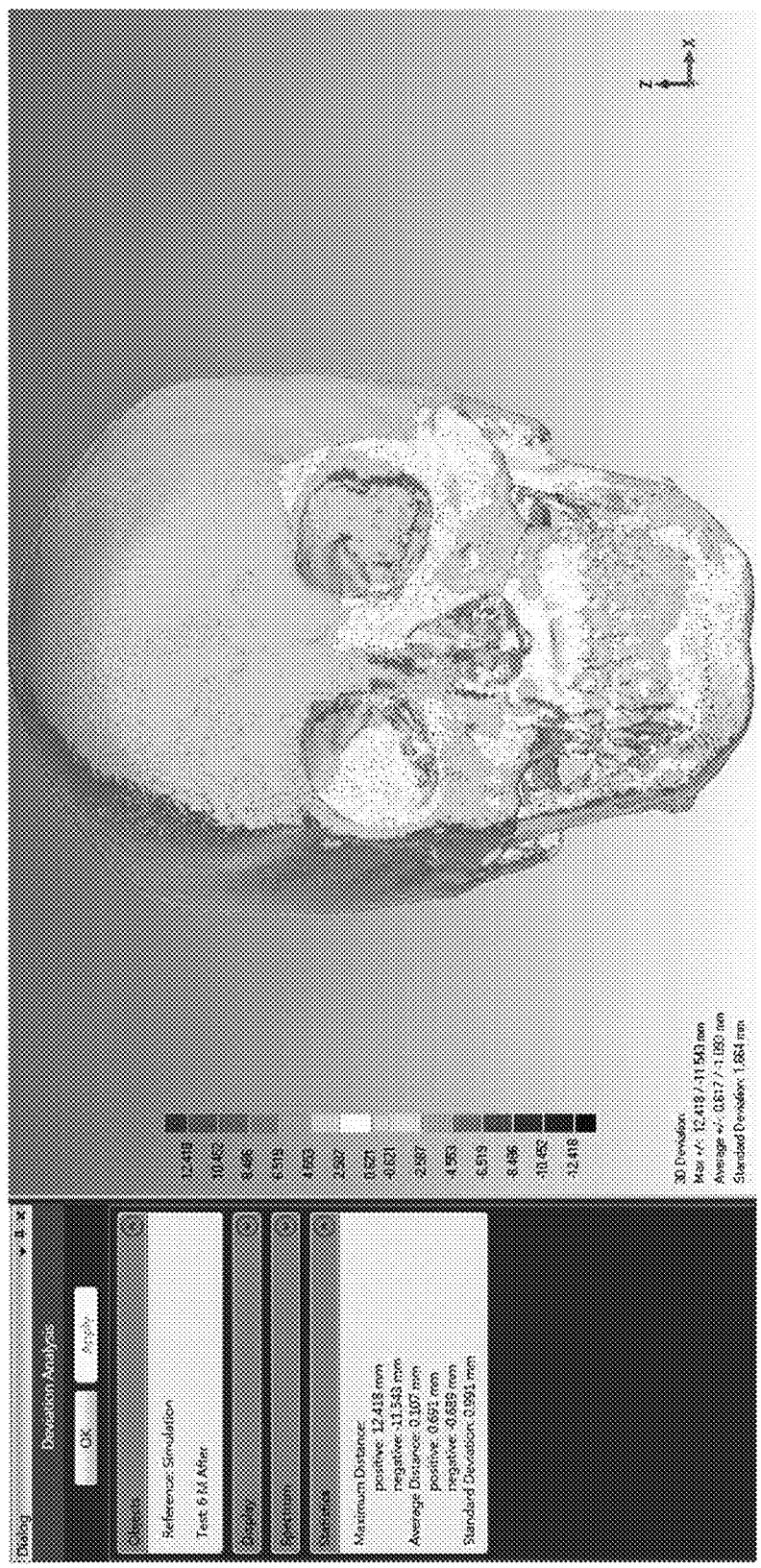
FIG. 18 shows a view of an oral and maxillofacial image simulation after surgery of an image correction design system for an oral and maxillofacial surgery of the invention.

Following the above-mentioned fifth embodiment, a first image data scanning module 1001, a second image data scanning module 1002, a scanning image correction and comparison module 1003 and an image block calculation module 1004 are executed with the same aspects as the above embodiments. Before a surgery is executed, a physician may use calculation data of a surgery simulation image design module 1005 to perform simulation comparison by inputting a surgery data parameter for the archives after the image layer management and cut block display of an image block calculation module 1004, so as to design and establish surgery simulation image files, wherein the surgery data parameter such as the related data of an operation site, skeleton moving distance, operation angle or dental impression overlap portion, etc. The surgery simulation image design module 1005 may further comprises a bone plate correction module 1050, wherein the surgery simulation image design module 1005 has a calculation data for inputting the simulation image file of the surgery portion to a 3D printing machine in order to make a rapid prototyping (RP) model having the same size and profile with a true head bone. Also, the calculation data of the surgery simulation image design module 1005 is used for correcting the bone plate correction module 1050. After correcting, a cutting guide bone plate or bending for fixing bone plate used before surgery is made to be a shape for using after surgery, or a fixing bone plate device for using after surgery is made by 3D printing or metallic laser additive manufacturing. Also, the bone plate combines to positioning hole, and marks on the model, shown as in FIG. 19. Also, each portion that is guided to cut according to the decision of a physician in the surgery and the position and accuracy of a fixing bone plate for occlusal upper jaw and lower jaw required by an orthodontic physician after surgery are adjusted. The surgery simulation image file that is calculated by the surgery simulation image design module 1005 and the bone plate correction module 1050 can be outputted to test and verify the accuracy before and after surgery for a physician and an orthodontic physician, and thus it can provide a correct image data accurately for simulation assessment before surgery or healing over confirmation after surgery by a physician, shown as a view of an oral and maxillofacial image simulation after surgery in FIG. 18. The result after surgery can be simulated by a physician and the time for performing the surgery can be shortened, and thus the success rate of surgery can be increased.

Figure 6:
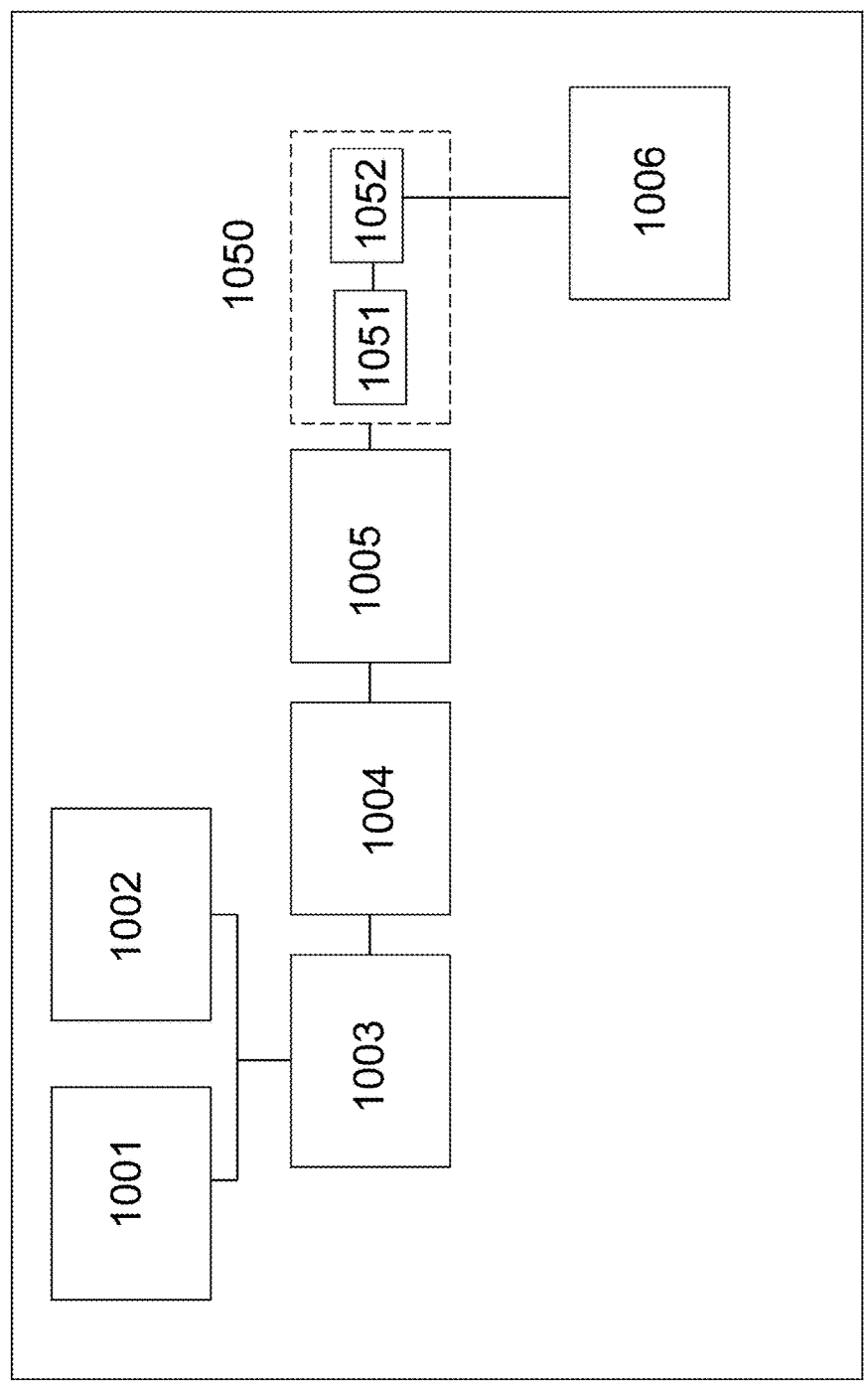
FIG. 6 shows a functional block diagram of a six embodiment of an image correction design system for an oral and maxillofacial surgery of the invention.

FIG. 6 shows a functional block diagram of a sixth embodiment of an image correction design system for an oral and maxillofacial surgery of the invention. The sixth embodiment also has a bone plate correction module 1050, and the bone plate correction module 1050 may further comprise a surgery guiding bone plate correction module 1051 and a fixing bone plate correction module 1052, wherein the surgery guiding bone plate correction module 1051 can provide the correction for surgery cutting area and the position correction for accurately drilling holes on a surgery guiding bone plate, and the fixing bone plate correction module 1052 can provide an accurate position of a fixing bone plate for skeleton healing over after surgery and the correction for the determined position of the skeleton. The others are executed with the same aspects as the fifth embodiment so the repeated description is omitted.

Figure 7:
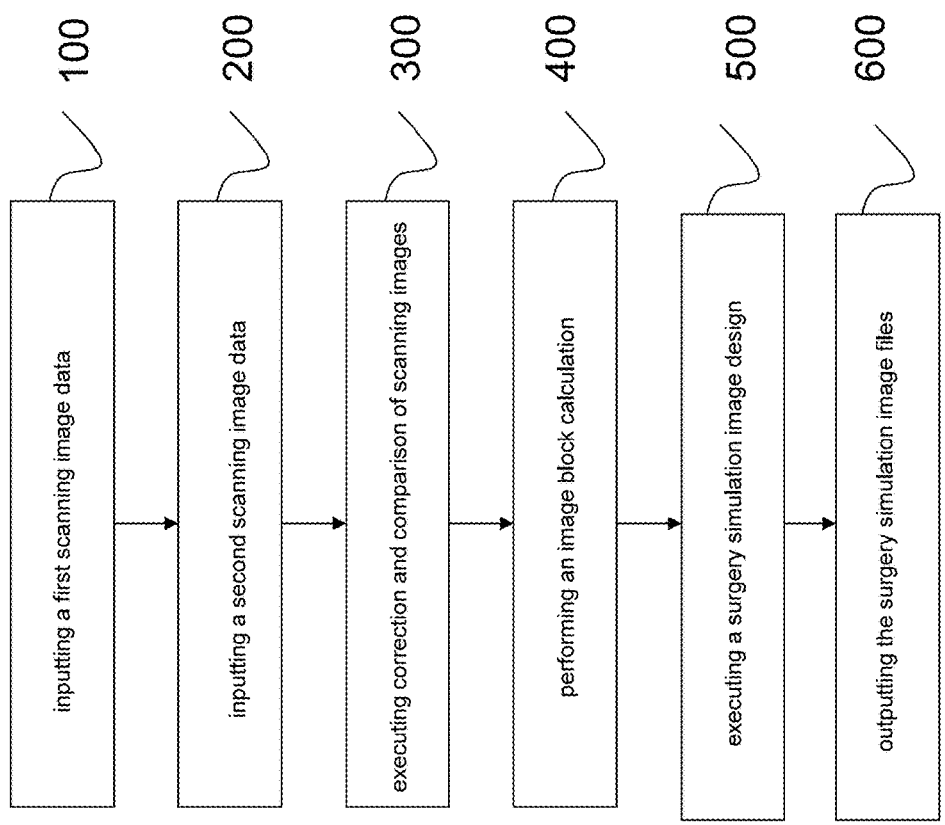
FIG. 7 shows a functional block diagram of a first embodiment of an image correction design method for an oral and maxillofacial surgery of the invention.

FIG. 7 shows a flow chart of a first embodiment of an image correction design method for an oral and maxillofacial surgery of the invention. The image correction design method for an oral and maxillofacial surgery comprises steps of: step 100, inputting a first scanning image data, wherein the first scanning image data is an image data of relative coordinate positions of maxillofacial bones, teeth, and soft tissues of a patient, and the first scanning image data is a computerized tomography scan file (CT file) or a 3 dimension data file; step 200, inputting a second scanning image data, wherein the second scanning image data is an image data of a plaster dental impression of a patient, and the second scanning image data is a 3 dimension data file; step 300, executing correction and comparison of scanning images for correcting and comparing the first scanning image data and the second scanning image data and performing archiving to obtain first archives; step 400, performing image block calculation, wherein the first archives of correction and comparison may perform an image layer management and block cutting display to obtain second archives, and the image layer management is separately displaying each portion that is cut according to the simulation surgery, and comparison calculation and block cutting display are performed by aligning the separately displaying images to an occlusal position of the image of the dental impression after the simulation surgery that is provided by an orthodontic physician; step 500, executing a surgery simulation image design by inputting a surgery data parameter for the second archives after the image layer management and cut block display, so as to design and establish surgery simulation image files, wherein the surgery data parameter such as the related data of an operation site, skeleton moving distance, operation angle or dental impression overlap portion, etc.; and step 600, outputting surgery simulation image files by a display device, and the display device is a LCD, Tablet PC, PDA or smartphone.

Figure 8:
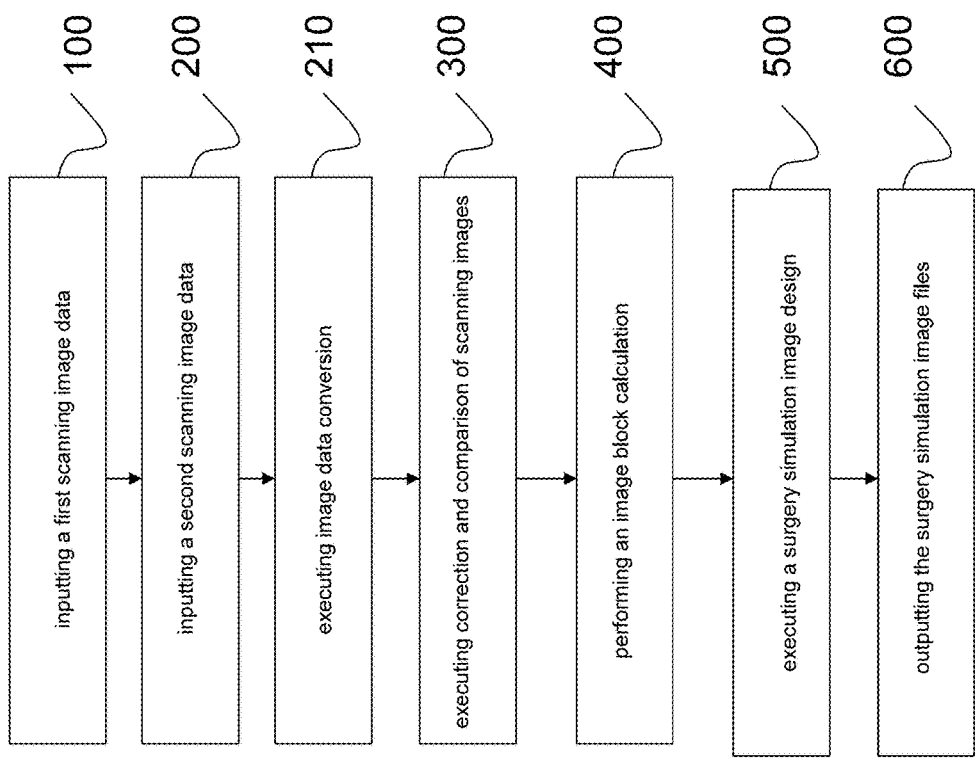
FIG. 8 shows a functional block diagram of a second embodiment of an image correction design method for an oral and maxillofacial surgery of the invention.

FIG. 8 shows a flow chart of a second embodiment of an image correction design method for an oral and maxillofacial surgery of the invention, wherein the steps are similar to the steps in FIG. 7. The second embodiment of an image correction design method further comprises a step 210 of executing image data conversion after step 100 of inputting a first scanning image data and step 200 of inputting a second scanning image data. The step 210 of executing image data conversion is used for converting the first scanning image data and the second scanning image data to 3 dimension data files. The format of the 3 dimension data file is a 3 dimension (3D) mechanical design STL file for using in the following steps. Next, step 300 of correction and comparison of scanning images is executed for correcting and comparing the first scanning image data and the second scanning image data and performing archiving to obtain first archives. Next, step 400 of image block calculation is performed, wherein the first archives of correction and comparison may perform an image layer management and block cutting display to obtain second archives, and the image layer management is separately displaying each portion that is cut according to the simulation surgery, and comparison calculation and block cutting display are performed by aligning the separately displaying images to an occlusal position of the image of the dental impression after the simulation surgery that is provided by an orthodontic physician. Next, step 500 of a surgery simulation image design is executed by inputting a surgery data parameter for the second archives after the image layer management and cut block display, so as to design and establish surgery simulation image files, wherein the surgery data parameter such as the related data of an operation site, skeleton moving distance, operation angle or dental impression overlap portion, etc. Also, the final step of step 600 of outputting surgery simulation image files is executed.

Figure 9:
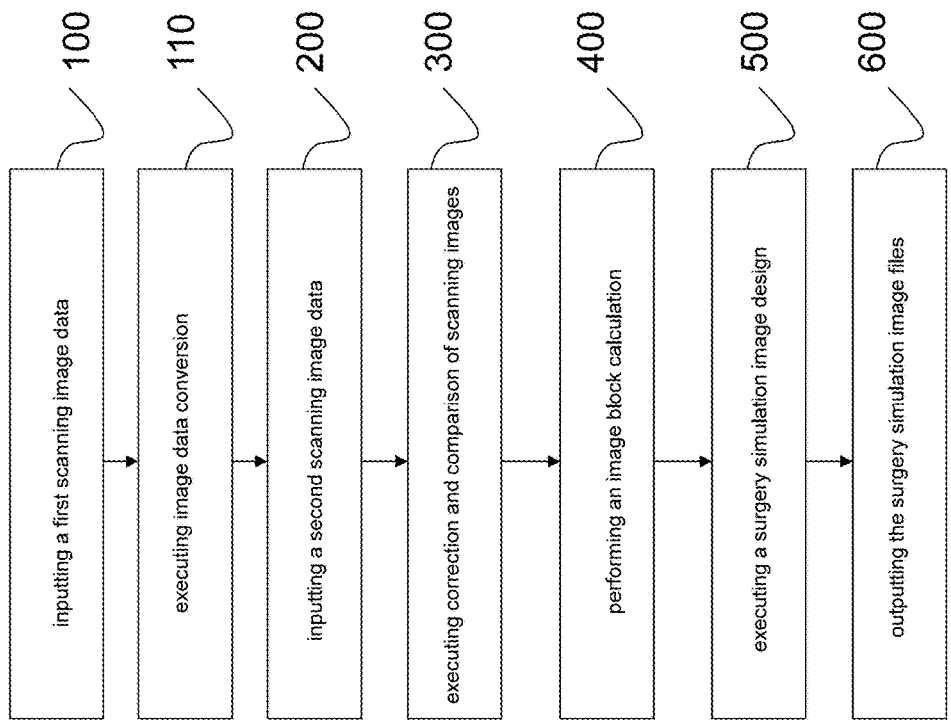
FIG. 9 shows a functional block diagram of a third embodiment of an image correction design method for an oral and maxillofacial surgery of the invention.

FIG. 9 shows a flow chart of a third embodiment of an image correction design method for an oral and maxillofacial surgery of the invention, wherein the steps are similar to the steps in FIG. 7. The third embodiment of an image correction design method further comprises a step 110 of executing image data conversion after step 100 of inputting a first scanning image data. The step 110 of executing image data conversion is used for converting the first scanning image data to a 3 dimension data file. Next, step 200 of inputting a second scanning image data is executed, wherein the second scanning image data is an image data of a plaster dental impression of a patient. Next, step 300 of correction and comparison of scanning images is executed for correcting and comparing the first scanning image data and the second scanning image data and performing archiving to obtain first archives. Next, step 400 of image block calculation is performed, wherein the first archives of correction and comparison may perform an image layer management and block cutting display to obtain second archives, and the image layer management is separately displaying each portion that is cut according to the simulation surgery, and comparison calculation and block cutting display are performed by aligning the separately displaying images to an occlusal position of the image of the dental impression after the simulation surgery that is provided by an orthodontic physician. Next, step 500 of a surgery simulation image design is executed by inputting a surgery data parameter for the second archives after the image layer management and cut block display, so as to design and establish surgery simulation image files, wherein the surgery data parameter such as the related data of an operation site, skeleton moving distance, operation angle or dental impression overlap portion, etc. Also, the final step of step 600 of outputting surgery simulation image files is executed.

Figure 10:
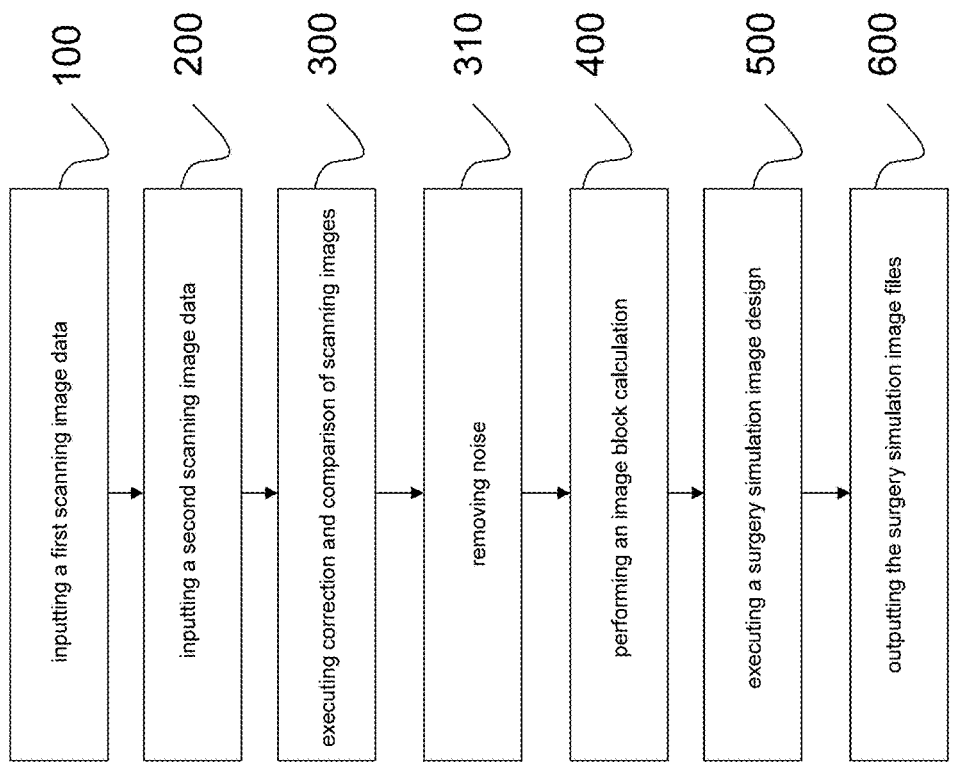
FIG. 10 shows a functional block diagram of a fourth embodiment of an image correction design method for an oral and maxillofacial surgery of the invention.

FIG. 10 shows a flow chart of a fourth embodiment of an image correction design method for an oral and maxillofacial surgery of the invention, wherein the steps are similar to the steps in FIG. 7. The fourth embodiment of an image correction design method further comprises a step 310 of removing noise after step 300 of correction and comparison of scanning images. The images treated by step 300 of executing correction and comparison of scanning images are likely to be affected by noise and other interference factors, so that the converted file is not true to the original or the image is vague. Therefore, the step 310 of removing noise is used for removing noise in the archive to obtain a true image data. Next, step 400 of image block calculation is performed, wherein the archives of correction and comparison may perform an image layer management and block cutting display, and the image layer management is separately displaying each portion that is cut according to the simulation surgery, and comparison calculation and block cutting display are performed by aligning the separately displaying images to an occlusal position of the image of the dental impression after the simulation surgery that is provided by an orthodontic physician. Next, step 500 of a surgery simulation image design is executed by inputting a surgery data parameter for the archives after the image layer management and cut block display, so as to design and establish surgery simulation image files, wherein the surgery data parameter such as the related data of an operation site, skeleton moving distance, operation angle or dental impression overlap portion, etc. Also, the final step of step 600 of outputting surgery simulation image files is executed.

Figure 11:
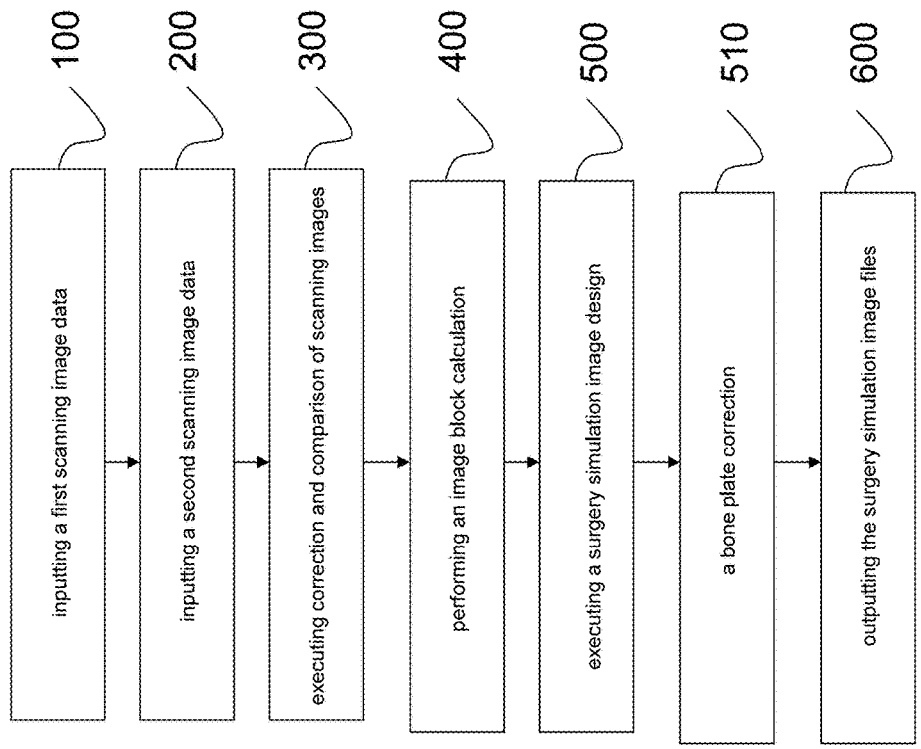
FIG. 11 shows a functional block diagram of a fifth embodiment of an image correction design method for an oral and maxillofacial surgery of the invention.

FIG. 11 shows a flow chart of a fifth embodiment of an image correction design method for an oral and maxillofacial surgery of the invention, wherein the steps are similar to the steps in FIG. 7. The fifth embodiment of an image correction design method further comprises a step 510 of a bone plate correction after the step 500 of a surgery simulation image design. The comparison of the surgery simulation image file and the step 510 of the bone plate correction is performed. When correction of the step 510 of the bone plate correction is performed, a cutting guide bone plate or bending for fixing bone plate used before surgery is made to be a shape for using after surgery, and a fixing bone plate device for using after surgery is made by 3D printing or metallic laser additive manufacturing. Also, the bone plate combines to positioning hole, and marks on the model. Also, each portion that is guided to cut according to the decision of a physician in the surgery and the position and accuracy of a fixing bone plate for occlusal upper jaw and lower jaw required by an orthodontic physician after surgery are adjusted and performing images archiving. The surgery simulation image file that is calculated by the step 500 of a surgery simulation image design and the step 510 of the bone plate correction can be outputted to test and verify the accuracy before and after surgery for a physician and an orthodontic physician, and thus it can provide a correct image data accurately for simulation assessment before surgery or healing over confirmation after surgery by a physician. The time for performing the surgery can be shortened, and thus the success rate of surgery can be increased. Also, the final step of a step 600 of outputting surgery simulation image files is executed.

Figure 12:
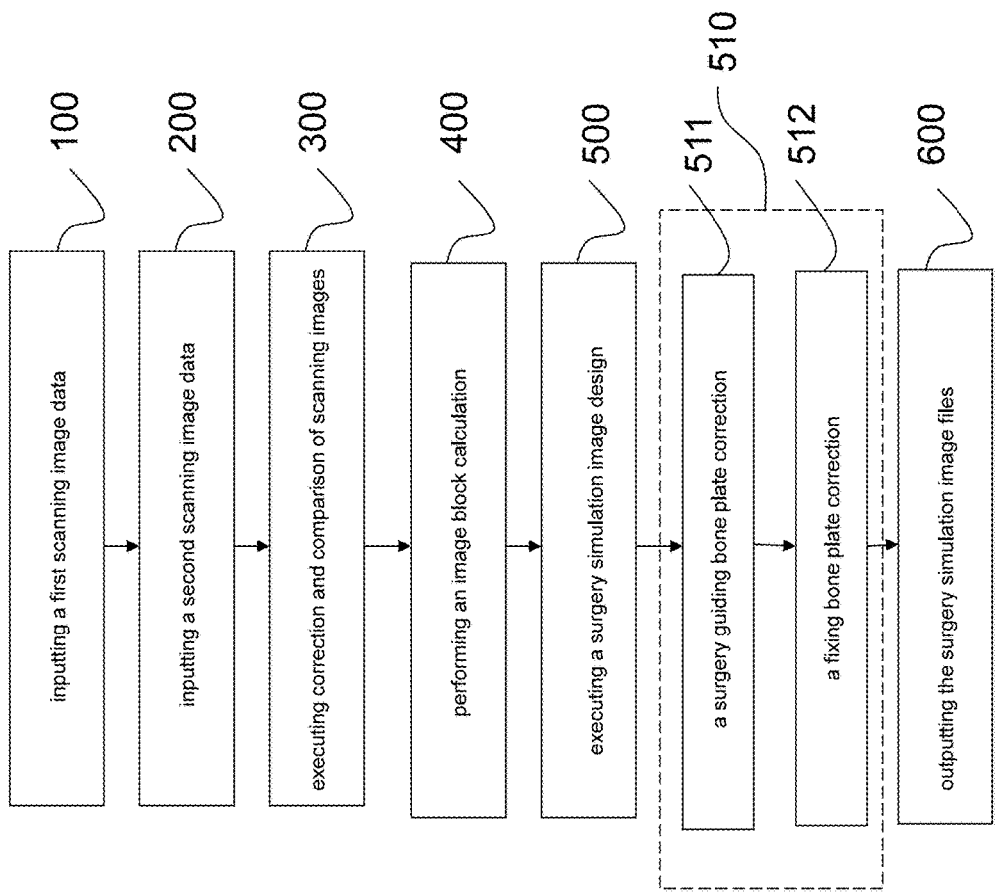
FIG. 12 shows a functional block diagram of a sixth embodiment of an image correction design method for an oral and maxillofacial surgery of the invention.

FIG. 12 shows a flow chart of a sixth embodiment of an image correction design method for an oral and maxillofacial surgery of the invention, wherein the step 510 of a bone plate correction comprises a step 511 of a surgery guiding bone plate correction and a step 512 of a fixing bone plate correction, wherein the step 511 of the surgery guiding bone plate correction can provide the correction for surgery cutting area and the position correction for accurately drilling holes on a surgery guiding bone plate, and the step 512 of the fixing bone plate correction can provide an accurate position of a fixing bone plate for skeleton healing over after surgery and the correction for the determined position of the skeleton. The others are executed with the same aspects as the fifth embodiment of an image correction design method for an oral and maxillofacial surgery so the repeated description is omitted.

It is to be understood by the those of ordinary skill in the art that the above description and the embodiments of the invention shown in the drawings are made only by way of example and not as a limitation of the scope of the invention. The purpose of the invention will become apparent from the detailed description and has been practiced effectively. The function and structural principle have been exhibited and described in the embodiments, and various possible modifications and alterations of the embodiments could be made, without departing from the principles of the invention.

What is claimed is:

1. An image correction design method for an oral and maxillofacial surgery comprising steps of:
    inputting a first scanning image data for scanning to obtain an image data of relative coordinate positions of maxillofacial bones, teeth, and soft tissues;
    inputting a second scanning image data for scanning an image data of a plaster dental impression of a patient;
    executing correction and comparison of scanning images for correcting and comparing the first scanning image data and the second scanning image data and performing archiving to obtain first archives;
    performing an image block calculation for performing an image layer management and block cutting display of the first archives to obtain second archives;
    executing a surgery simulation image design for inputting a surgery data parameter for the second archives after the image layer management and cut block display, so as to design and establish surgery simulation image files; and
    outputting the surgery simulation image files by using a display device.

2. The image correction design method for an oral and maxillofacial surgery according to claim 1, further comprising a step of executing image data conversion used for converting the first scanning image data and the second scanning image data to 3 dimension data files.

3. The image correction design method for an oral and maxillofacial surgery according to claim 1, further comprising a step of executing image data conversion after the step of inputting a first scanning image data, and the step of executing image data conversion is used for converting the first scanning image data to a 3 dimension data file.

4. The image correction design method for an oral and maxillofacial surgery according to claim 2, wherein each the 3 dimension data files has a format of a 3 dimension (3D) mechanical design STL file.

5. The image correction design method for an oral and maxillofacial surgery according to claim 1, wherein the first scanning image data is a computerized tomography scan file (CT file).

6. The image correction design method for an oral and maxillofacial surgery according to claim 1, wherein the second scanning image data is an image data of a plaster dental impression of a patient scanned by a precise grating instrument.

7. The image correction design method for an oral and maxillofacial surgery according to claim 1, further comprising a step of removing noise after the step of executing a scanning image correction and comparison, and the step of removing noise is used for removing noise in the archive.

8. The image correction design method for an oral and maxillofacial surgery according to claim 1, further comprising a step of a bone plate correction for performing a comparison of the surgery simulation image file and the step of the bone plate correction.

9. The image correction design method for an oral and maxillofacial surgery according to claim 8, wherein the step of a bone plate correction comprises a step of a surgery guiding bone plate correction and a step of a fixing bone plate correction.

10. The image correction design method for an oral and maxillofacial surgery according to claim 1, wherein the surgery data parameter is a moving distance of the oral and maxillofacial skeleton, an operation cutting angle or a skeleton overlap portion.

11. The image correction design method for an oral and maxillofacial surgery according to claim 1, wherein the display device is a LCD, Tablet PC, PDA or smartphone.

12. An image correction design system for an oral and maxillofacial surgery, comprising:
    a first image data scanning module for scanning to obtain an image data of relative coordinate positions of maxillofacial bones, teeth, and soft tissues;
    a second image data scanning module for scanning an image data of a plaster dental impression of a patient;
    a scanning image correction and comparison module for correcting and comparing the image data from the first image data scanning module and the image data from the second image data scanning module and performing archiving to obtain first archives;
    an image block calculation module for performing an image layer management and block cutting display of the first archives to obtain second archives;
    a surgery simulation image design module for inputting a surgery data parameter for the second archives after the image layer management and cut block display, so as to design and establish surgery simulation image files; and
    an output module for outputting the surgery simulation image files by using a display device.

13. The image correction design system for an oral and maxillofacial surgery according to claim 12, further comprising an image data conversion module used for converting the image data of the first image data scanning module and the image data of the second image data scanning module to 3 dimension data files.

14. The image correction design system for an oral and maxillofacial surgery according to claim 12, wherein the first image data scanning module further comprises an image data conversion module used for converting the image data of the first image data scanning module to a 3 dimension data file.

15. The image correction design system for an oral and maxillofacial surgery according to claim 13, wherein each the 3 dimension data files has a format of a 3 dimension (3D) mechanical design STL file.

16. The image correction design system for an oral and maxillofacial surgery according to claim 12, wherein the image data of the first image data scanning module is a computerized tomography scan file (CT file).

17. The image correction design system for an oral and maxillofacial surgery according to claim 12, wherein the image data of the second image data scanning module is an image data of a plaster dental impression of a patient scanned by a high precise grating instrument.

18. The image correction design system for an oral and maxillofacial surgery according to claim 12, wherein the scanning image correction and comparison module further comprises a noise removing module used for removing noise in the archive.

19. The image correction design system for an oral and maxillofacial surgery according to claim 12, further comprising a bone plate correction module for performing a comparison of the surgery simulation image file and the data of the bone plate correction module.

20. The image correction design system for an oral and maxillofacial surgery according to claim 19, wherein the bone plate correction module comprises a surgery guiding bone plate correction module and a fixing bone plate correction module.

21. The image correction design system for an oral and maxillofacial surgery according to claim 12, wherein the surgery data parameter is a moving distance of the oral and maxillofacial skeleton, an operation cutting angle or a skeleton overlap portion.

22. The image correction design system for an oral and maxillofacial surgery according to claim 12, wherein the display device is a LCD, Tablet PC, PDA or smartphone.

23. The image correction design method for an oral and maxillofacial surgery according to claim 3, wherein each the 3 dimension data files has a format of a 3 dimension (3D) mechanical design STL file.

24. The image correction design system for an oral and maxillofacial surgery according to claim 14, wherein each the 3 dimension data files has a format of a 3 dimension (3D) mechanical design STL file.

* * * * *